(12) United States Patent
Foulon et al.

(10) Patent No.: US 7,488,743 B2
(45) Date of Patent: Feb. 10, 2009

(54) INDOLIN-2-ONE PYRIDINE DERIVATIVES, PREPARATION AND THERAPEUTIC USE THEREOF

(75) Inventors: Loïc Foulon, Portet sur Garonne (FR); Claudine Serradeil-Le Gal, Escalquens (FR); Gérard Valette, Lacroix-Falgarde (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/686,977

(22) Filed: Mar. 16, 2007

(65) Prior Publication Data
US 2007/0185166 A1 Aug. 9, 2007

Related U.S. Application Data

(63) Continuation of application No. PCT/FR2005/002316, filed on Sep. 19, 2005.

(30) Foreign Application Priority Data
Sep. 20, 2004 (FR) .................................. 04 09906

(51) Int. Cl.
*A61K 31/4439* (2006.01)
*C07D 401/14* (2006.01)

(52) U.S. Cl. .................................. 514/339; 546/277.7
(58) Field of Classification Search .............. 546/277.7; 514/339
See application file for complete search history.

(56) References Cited

U.S. PATENT DOCUMENTS

| 4,882,329 A | 11/1989 | Lerch et al. |
| 5,594,023 A | 1/1997 | Wagnon et al. |
| 2004/0059132 A1 | 3/2004 | Foulon et al. |

FOREIGN PATENT DOCUMENTS

| AU | 684791 | 4/1998 |
| EP | 0212481 | 3/1987 |
| EP | 0636608 | 2/1995 |
| WO | WO 95/18105 | 7/1995 |
| WO | WO 01/74775 | 10/2001 |

OTHER PUBLICATIONS

Vippagunta et al., "Crystalline Solid", Advanced Drug Delivery Reviews 48 (2001) 3-26.*
Guillory (in Brittain ed), "Polymorphism, etc.," NY: Marcel Dekker, Inc., 1999, 183-226.*

* cited by examiner

*Primary Examiner*—Patricia L Morris
(74) *Attorney, Agent, or Firm*—Kelly L. Bender

(57) ABSTRACT

The disclosure concerns indolin-2-one pyridine compounds of general formula (I):

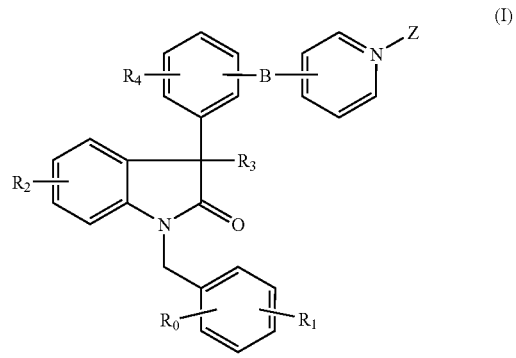

wherein $R_0$, $R_1$, $R_2$, $R_3$, $R_4$, Z and B have the meanings given in the description, and pharmaceutically acceptable salts thereof; and also pharmaceutical compositions comprising, processes for making and methods of using said compounds.

11 Claims, No Drawings

INDOLIN-2-ONE PYRIDINE DERIVATIVES, PREPARATION AND THERAPEUTIC USE THEREOF

The subject-matter of the present invention is indolin-2-one pyridine derivatives, their preparation and their therapeutic application.

Several compounds having an activity with regard to oxytocin receptors are known. Indolin-2-one derivatives, which are ligands of oxytocin receptors, have been disclosed in particular in the document WO 01/74775.

However, there still exists a need to find novel ligands with an affinity for and which are selective for oxytocin receptors. Indolin-2-one pyridine derivatives have now been found which are ligands with an affinity for and which are selective for oxytocin receptors.

A subject matter of the present invention is compounds corresponding to the formula (I):

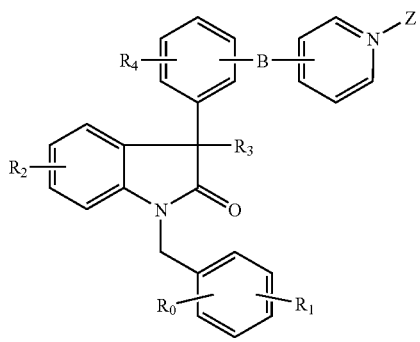

in which:
$R_0$ represents a hydrogen atom, a halogen atom, a $(C_1-C_6)$ alkyl group or a $(C_1-C_6)$ alkoxy group;
$R_1$ represents a hydrogen atom, a halogen atom, a $(C_1-C_6)$ alkyl group or a $(C_1-C_6)$ alkoxy group;
$R_2$ represents a hydrogen atom, a halogen atom, a $(C_1-C_6)$ alkyl group or a $(C_1-C_6)$ alkoxy group;
$R_3$ represents a hydrogen atom or a $(C_1-C_6)$ alkyl group;
$R_4$ represents a hydrogen atom, a halogen atom, a $(C_1-C_6)$ alkyl group or a $(C_1-C_6)$ alkoxy group;
Z represents:
  an oxygen atom,
  a $(C_1-C_6)$ alkyl group optionally substituted by one or more groups chosen from: hydroxyl, $(C_1-C_6)$ alkoxy, —COOR, in which R represents a hydrogen atom or a $(C_1-C_3)$ alkyl group, or —CONRR', in which R and R' represent, independently of one another, a hydrogen atom or a $(C_1-C_3)$ alkyl group or else R and R' form, together with the nitrogen atom to which they are bonded, a pyrrolidinyl, piperidinyl or morpholinyl group;
  a tetrahydrofuranyl group or a tetrahydropyranyl group, said groups optionally being substituted by one or more $(C_1-C_3)$ alkyl, hydroxyl or carboxyl groups or a —$CH_2OH$ group;
B represents a T-W group, in which:
  T represents a —$(CH_2)_m$— group, it being possible for m to be equal to 0 or 1;
  W represents:
  a —$CONR_6R_7$ group, in which:
    $R_6$ represents a hydrogen atom or a $(C_1-C_6)$ alkyl group,
    $R_7$ represents a $(C_1-C_6)$ alkylene group;
  an —$NR_8COR_9$ group, in which:
    $R_8$ represents a hydrogen atom or a $(C_1-C_6)$ alkyl group,
    $R_9$ represents a —$(CH_2)_n$— group, it being possible for n to take values from 0 to 3;

in the form of the base or in the form of a pharmaceutically acceptable salt, in the hydrate or solvate form, and its enantiomers, diastereoisomers and their mixtures.

The compounds of formula (I) can comprise one or more asymmetric carbon atoms. They can thus exist in the form of enantiomers or of diastereoisomers. These enantiomers or diastereoisomers, and their mixtures, including the racemic mixtures, form part of the invention.

The compounds of the invention can also exist in the form of bases or of addition salts of acids, in the hydrate or solvate form.

In the context of the present invention:
  the term "a halogen atom" is understood to mean a fluorine, a chlorine, a bromine or an iodine,
  the terms "a $(C_1-C_3)$ alkyl group" and "a $(C_1-C_6)$ alkyl group" are understood to mean a saturated, linear or branched, aliphatic group respectively comprising from 1 to 3 or from 1 to 6 carbon atoms. Mention may be made, for example, of the methyl, ethyl, propyl, isopropyl, butyl, isobutyl, tert-butyl or pentyl groups, it being possible for said abovementioned alkyl groups optionally to be substituted,
  the term "a $(C_1-C_6)$ alkylene group" is understood to mean a saturated, linear or branched, divalent alkyl group comprising from 1 to 6 carbon atoms. Mention may be made, for example, of the methylene, ethylene, 1-methylethylene or propylene groups,
  the term "a $(C_1-C_6)$ alkoxy group" is understood to mean a saturated, linear or branched, aliphatic group which can comprise from 1 to 6 carbon atoms, as defined above, bonded to an oxygen atom. Mention may be made, for example, of a methoxy or ethoxy group,
  the term "a tetrahydrofuranyl group" is understood to mean a tetrahydrofuran-2-yl or tetrahydrofuran-3-yl group, it being possible for said abovementioned groups optionally to be substituted,
  the term "a tetrahydropyranyl group" is understood to mean a tetrahydropyran-2-yl, tetrahydropyran-3-yl or tetrahydropyran-4-yl group, it being possible for said abovementioned groups optionally to be substituted.

Mention may be made, among the compounds which are a subject matter of the invention, of a first group of compounds of formula (I) in which:
$R_0$ represents a $(C_1-C_6)$ alkoxy group, in particular a methoxy group in the 2-position of the phenyl;
$R_1$ represents a $(C_1-C_6)$ alkoxy group, in particular a methoxy group in the 4-position of the phenyl;
$R_2$, $R_3$, $R_4$, Z and B are as defined above; in the form of the base or in the form of a pharmaceutically acceptable salt, in the hydrate or solvate form, and its enantiomers, diastereoisomers and their mixtures.

Mention may be made, among the compounds which are a subject matter of the invention, of a second group of compounds of formula (I) in which:
$R_0$ represents a hydrogen atom, a halogen atom, a $(C_1-C_6)$ alkyl group or a $(C_1-C_6)$ alkoxy group;
$R_1$ represents a hydrogen atom, a halogen atom, a $(C_1-C_6)$ alkyl group or a $(C_1-C_6)$ alkoxy group;
$R_2$, $R_3$, $R_4$ and B are as defined above;
Z represents an oxygen atom;

in the form of the base or in the form of a pharmaceutically acceptable salt, in the hydrate or solvate form, and its enantiomers, diastereoisomers and their mixtures.

Mention may be made, among the compounds which are a subject matter of the invention, of a third group of compounds of formula (I), in which:
$R_0$ represents a hydrogen atom, a halogen atom, a ($C_1$-$C_6$)alkyl group or a ($C_1$-$C_6$)alkoxy group;
$R_1$ represents a hydrogen atom, a halogen atom, a ($C_1$-$C_6$)alkyl group or a ($C_1$-$C_6$)alkoxy group;
$R_2$, $R_3$, $R_4$ and B are as defined above;
Z represents:
a ($C_1$-$C_6$)alkyl group optionally substituted by one or more groups chosen from: hydroxyl, ($C_1$-$C_6$)alkoxy, —COOR, in which R represents a hydrogen atom or a ($C_1$-$C_3$)alkyl group, or —CONRR', in which R and R' represent, independently of one another, a hydrogen atom or a ($C_1$-$C_3$)alkyl group or else R and R' form, together with the nitrogen atom to which they are bonded, a pyrrolidinyl, piperidinyl or morpholinyl group;
a tetrahydrofuranyl group, in particular a tetrahydrofuran-2-yl group, or a tetrahydropyranyl group, in particular a tetrahydropyran-2-yl group, said groups optionally being substituted by one or more ($C_1$-$C_3$)alkyl, hydroxyl or carboxyl groups or a —$CH_2OH$ group;

in the form of the base or in the form of a pharmaceutically acceptable salt, in the hydrate or solvate form, and its enantiomers, diastereoisomers and their mixtures.

Mention may be made, among the compounds which are a subject matter of the invention, of a fourth group of compounds chosen from:
3-[({4-chloro-3-[5-chloro-1-(2,4-dimethoxybenzyl)-3-methyl-2-oxo-2,3-dihydro-1H-indol-3-yl]benzoyl}(ethyl)amino)methyl]-1-(2-hydroxyethyl)pyridinium chloride
1-carboxymethyl-3-[({4-chloro-3-[5-chloro-1-(2,4-dimethoxybenzyl)-3-methyl-2-oxo-2,3-dihydro-1H-indol-3-yl]benzoyl}(ethyl)amino)methyl]pyridinium chloride,
1-(β-D-glucopyranuronosyl)-3-[({4-chloro-3-[5-chloro-1-(2,4-dimethoxybenzyl)-3-methyl-2-oxo-2,3-dihydro-1H-indol-3-yl]benzoyl}(ethyl)amino)methyl]pyridinium chloride,
3-[({4-chloro-3-[5-chloro-1-(2,4-dimethoxybenzyl)-3-methyl-2-oxo-2,3-dihydro-1H-indol-3-yl]benzoyl}(ethyl)amino)methyl]-1-(D-glucopyranosyl)pyridinium chloride,
3-[({4-chloro-3-[5-chloro-1-(2,4-dimethoxybenzyl)-3-methyl-2-oxo-2,3-dihydro-1H-indol-3-yl]benzoyl}(ethyl)amino)methyl]-1-(D-galactopyranosyl)pyridinium chloride,
4-chloro-3-[5-chloro-1-(2,4-dimethoxybenzyl)-3-methyl-2-oxo-2,3-dihydro-1H-indol-3-yl]-N-ethyl-N-(1-oxypyrid-3-ylmethyl)benzamide,
4-chloro-3-[5-chloro-1-(2,4-dimethoxybenzyl)-3-methyl-2-oxo-2,3-dihydro-1H-indol-3-yl]-N-ethyl-N-(1-oxypyrid-3-ylmethyl)benzamide hydrochloride,
(+)-4-chloro-3-[5-chloro-1-(2,4-dimethoxybenzyl)-3-methyl-2-oxo-2,3-dihydro-1H-indol-3-yl]-N-ethyl-N-[3-(1-oxypyridin-4-yl)propyl]benzamide.

Another subject matter of the invention is a process for the preparation of the compounds of formula (I).

According to a general method of preparation of the compounds of formula (I), the compound of following formula (II):

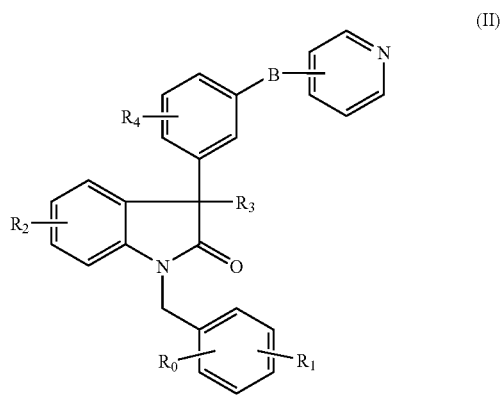

in which $R_0$, $R_1$, $R_2$, $R_3$, $R_4$ and B are as defined above, is reacted with a peracid or a compound of formula Z-X, in which Z is as defined above and X represents a leaving group.

The term "leaving group" is understood to mean a group which can be easily replaced by another group during a substitution reaction, for example. Examples of leaving groups and preparation references are given in "Advanced Organic Chemistry", J. March, 3rd Edition, Wiley Interscience, pp. 310-316. Mention may be made, by way of indication, of a halogen atom or an activated hydroxyl group, such as a mesylate, tosylate, triflate, acetate, a sulfonate or an imidate.

The precursor compounds of formula (II) are described in the document WO 01/74775. When the compounds of formula (II) are not specifically described in the document WO 01/74775, these compounds are prepared analogously according to methods described in document WO 01/74775 or according to methods described in the literature and known to a person skilled in the art.

Thus, in order to obtain a compound of formula (I) in which Z represents an oxygen atom, a compound of formula (II) as defined above is reacted with an oxidizing derivative, such as an aliphatic organic peracid or an aromatic peracid. Mention may be made, among aliphatic organic peracids, for example, of peracetic acid, performic acid, perlauric acid or perphthalic acid. Mention may be made, among aromatic peracids, for example, of perbenzoic acids or their derivatives, such as 3-chloroperbenzoic acid. The reaction takes place at temperatures of between 0° C. and 90° C., preferably at temperatures of less than 50° C.

These acids can be used as is when they are stable or can be generated in situ by reaction of hydrogen peroxide with the carboxylic acid or anhydride under consideration. Thus, peracetic acid is obtained by reaction of a 30-40% aqueous hydrogen peroxide solution with glacial acetic acid, and perphthalic acid or permaleic acid is obtained by reaction of hydrogen peroxide with the corresponding anhydrides. It is also possible to proceed according to methods described in "Heterocyclic N-oxides", *CRC Press* (1991), Albini A. and Pietra S.

The peracids are chosen in particular from anhydrous peracids and are used in anhydrous solvents, such as aliphatic or aromatic hydrocarbons, halogenated solvents, dioxane or dimethoxyethane, or aliphatic or aromatic nitriles.

The final compounds are isolated as is or are converted to salts by reaction with a strong acid, such as hydrochloric acid, hydrobromic acid, sulfuric acid or a sulfonic acid, such as methanesulfonic acid, for example, in solvents such as ethers, alcohols or their mixture.

In order to obtain a compound of formula (I) in which Z represents a $(C_1-C_6)$alkyl group optionally substituted by one or more groups chosen from: hydroxyl, $(C_1-C_6)$alkoxy, —COOR, in which R represents a hydrogen atom or a $(C_1-C_3)$alkyl group, or —CONRR', in which R and R' represent, independently of one another, a hydrogen atom or a $(C_1-C_3)$ alkyl group or else R and R' form, together with the nitrogen atom to which they are bonded, a pyrrolidinyl, piperidinyl or morpholinyl group, a compound of formula (II) is reacted with a reactive derivative of Z: Z-X, in which Z is as defined in the above and X represents a leaving group, such as a halogen atom, a triflate or a sulfonate. The reaction takes place at temperatures of between 0° C. and 110° C., in solvents such as aromatic hydrocarbons, aliphatic ethers, alcohols, preferably in ketones, such as acetone, aprotic amides, such as dimethylformamide, and aliphatic nitriles, such as acetonitrile.

The functional groups capable of reacting, such as amines, alcohols or carboxylic acids, are protected by a protective group and then deprotected after reaction according to methods well known to a person skilled in the art.

The term "protective group" is understood to mean a group which makes it possible, on the one hand, to protect a reactive functional group, such as a hydroxyl or carboxyl group or an amine, during a synthesis and, on the other hand, to regenerate the reactive functional group intact at the end of the synthesis. Examples of protective groups and protection and deprotection methods are given in Protective Groups in Organic Synthesis, T. W. Greene and P. G. M. Wuts, 3rd Ed. (John Wiley and Sons Inc., New York, 1999).

The counterions generated by the reaction can be retained or exchanged by operating, for example, on ion-exchange resins.

It is also possible to proceed according to the methods described in "The Chemistry of Heterocyclic Compounds, Pyridine and its Derivatives", Part two (Quaternary Pyridinium Compounds), Interscience Publishers (1962).

In order to obtain a compound of formula (I) in which Z represents a tetrahydrofuranyl group or a tetrahydropyranyl group, said groups optionally being substituted by one or more $(C_1-C_3)$alkyl, hydroxyl or carboxyl groups or a —CH$_2$OH group, the operation is carried out according to the principle described above, in particular by reacting a compound of formula (II) as defined above with a reactive derivative of Z: Z-X, in which Z is as defined above and X represents a leaving group, such as a halogen or a triflate, acetate, imidate, thioalkyl or thioaryl group, according to the methods described by G. S. Boons, *Tetrahedron* (1996), 52, pp. 1095-1121.

The reaction takes place at temperatures of between 50 and 110° C. in rigorously anhydrous solvents, such as acetonitrile (*JOC* (2000), 65, pp. 8197-8203), or in nitromethane in the presence of cadmium carbonate, as described in *J. Med. Chem.* (1988), 31, pp. 1295-1305, and in *Chem. Pharm. Bull.* (1987), 35 (9), pp. 3975-3978.

In the case where Z exhibits functional groups capable of reacting, such as hydroxyl functional groups, the latter are protected by acyl groups, such as benzoyl groups or acetyl, according to conventional techniques known to a person skilled in the art. The hydroxyl functional groups are subsequently deprotected, either in an acidic medium with a solution of hydrobromic acid in an alcohol (*JOC* (2000), 65, pp. 8197-8203) or tetrafluoroboric acid in methanol (*JACS* (1988), 120 (16), pp. 3887-3893) or of trifluoromethanesulfonic acid in acetonitrile (*Bioorg. Med. Chem. Lett.* (2002), 12 (8), pp. 1135-1138) or in a basic medium with a solution of ammonia in methanol (*Chem. Commun.* (1999), 8, pp. 729-730, and *J. Med. Chem.* (1988), 31, pp. 1295-1305).

It is also possible to operate by conventional saponification in an alcohol comprising aqueous sodium hydroxide, followed by acidification with hydrochloric acid.

The counterions generated by the reaction can be retained or exchanged by operating, for example, on ion-exchange resins.

The following examples illustrate the present invention without limiting the scope thereof.

In what follows:

M.p.=melting point (in degrees Celsius), measured on a Kofler bench.

MS=mass spectrum, produced on a quadrupole spectrometer of Platform LCZ type (Waters) or of ZQ 4000 type (Waters) in positive electrospray ionization mode.

NMR=nuclear magnetic resonance, the spectrum of which is produced on a Fourier transform spectrometer (Bruker) at a temperature of 300 K.

s=singlet, t=triplet, m=multiplet,

DMSO=dimethyl sulfoxide,

CDCl$_3$=deuterated chloroform

EXAMPLE 1

3-[({4-Chloro-3-[5-chloro-1-(2,4-dimethoxybenzyl)-3-methyl-2-oxo-2,3-dihydro-1H-indol-3-yl]benzoyl}(ethyl)amino)methyl]-1-(2-hydroxyethyl)pyridinium chloride (I): $R_0$=2-MeO; $R_1$=4-MeO; $R_2$=5-Cl; $R_3$=Me; $R_4$=4-Cl;

$$B = -\overset{O}{\underset{}{C}} - N \begin{matrix} -CH_3 \\ -A \end{matrix} \qquad A = \text{3-pyridinium-N-(2-hydroxyethyl)}$$

Stage 1.1

4-Chloro-3-[5-chloro-1-(2,4-dimethoxybenzyl)-3-methyl-2-oxo-2,3-dihydro-1H-indol-3-yl]-N-ethyl-N-(pyridin-3-ylmethyl)benzamide 4-Chloro-3-[5-chloro-1-(2,4-dimethoxybenzyl)-3-methyl-2-oxoindolin-3-yl]benzoic acid, in the racemic form, is treated with N-ethyl-3-pyridylmethylamine (document WO 01/074775, example 201a) and b)). 4-Chloro-3-[5-chloro-1-(2,4-dimethoxybenzyl)-3-methyl-2-oxoindolin-3-yl]benzoic acid, in the racemic form, is described in the document WO 01/074775, in example 101. After silica chromatography, elution being carried out with a dichloromethane/methanol 90/10 mixture, the expected compound, in the racemic form, is obtained crystallized from methanol (white powder).

M.p.=98° C. (0.5H$_2$O)

Stage 1.2:

3-[({4-Chloro-3-[5-chloro-1-(2,4-dimethoxybenzyl)-3-methyl-2-oxo-2,3-dihydro-1H-indol-3-yl]benzoyl}(ethyl)amino)methyl]-1-(2-hydroxyethyl)pyridinium chloride The mixture of 0.2 g of the amide prepared in stage 1.1 in the presence of 0.54 g of 2-chloroethanol in 2 ml of acetonitrile is heated at reflux for 3 days under an inert atmosphere. After evaporating the solvent under vacuum, purification is carried out by C18 reverse phase silica preparative chromatography, elution being carried out with an acetonitrile/water gradient from 20/80 to 80/20, and the solution obtained is lyophilized after freezing.

The expected product is obtained in the form of a white powder.

MS [(+)ESI, m/z]=648 (M$^+$).

$^1$H NMR 250 MHz (CDCl$_3$): 1.35 (t, 3H); 1.81 (s, 3H); 3.61 (m, 2H); 3.62 (s, 3H); 3.90 (s, 3H); 4.10 (t, 2H); 4.70-5.2 (m, 6H); 6.4-9 (m, 13H).

EXAMPLE 2

1-Carboxymethyl-3-[({4-chloro-3-[5-chloro-1-(2,4-dimethoxybenzyl)-3-methyl-2-oxo-2,3-dihydro-1H-indol-3-yl]benzoyl}(ethyl)amino)methyl]pyridinium chloride (I): R$_0$=2-MeO; R$_1$=4-MeO; R$_2$=5-Cl; R$_3$=Me; R$_4$=4-Cl;

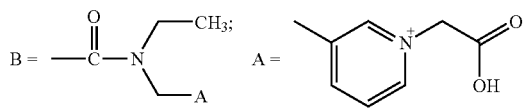

The expected compound is obtained under the same conditions as those of example 1 from 4-chloro-3-[5-chloro-1-(2,4-dimethoxybenzyl)-3-methyl-2-oxo-2,3-dihydro-1H-indol-3-yl]-N-ethyl-N-(pyridin-3-ylmethyl)benzamide, in the racemic form, prepared in stage 1.1 of example 1, and from chloroacetic acid.

MS [(+)ESI, m/z]=662 (M$^+$).

$^1$H NMR 400 MHz (CDCl$_3$): 1.27 (t, 3H); 1.80 (s, 3H); 3.52 (m, 2H); 3.80 (s, 3H); 3.88 (s, 3H); 4.76 (d, 1H); 4.90 (s, 2H); 5.12 (d, 1H); 5.47 (s, 2H); 6.40-9.4 (m, 13H).

EXAMPLE 3

1-(β-D-Glucopyranuronosyl)-3-[({4-chloro-3-[5-chloro-1-(2,4-dimethoxybenzyl)-3-methyl-2-oxo-2,3-dihydro-1H-indol-3-yl]benzoyl}(ethyl)amino)methyl]pyridinium chloride (I): R$_0$=2-MeO; R$_1$=4-MeO; R$_2$=5-Cl; R$_3$=Me; R$_4$=4-Cl;

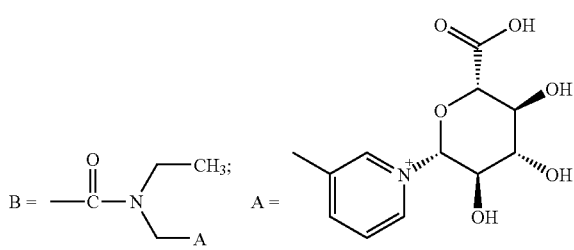

Stage 3.1:

3-[({4-Chloro-3-[5-chloro-1-(2,4-dimethoxybenzyl)-3-methyl-2-oxo-2,3-dihydro-1H-indol-3-yl]benzoyl}(ethyl)amino)methyl]-1-(methyl-2,3,4-triacetyl-β-D-glucopyranuronosyl)pyridinium bromide 100 mg of the compound of example 201 described in patent WO 01/074775 are heated at reflux for 10 minutes under an inert atmosphere in the presence of 131 mg of methyl acetobromo-α-D-glucuronate and 43 mg of cadmium carbonate in 1 ml of nitromethane. After evaporating the solvent under vacuum, the residue is chromatographed on silica, elution being carried out with a dichloromethane/methanol 95/5 mixture. The expected product is obtained in the form of an orange-colored powder.

MS [(+)ESI, m/z]=920 (M$^+$).

Stage 3.2:

1-(β-D-Glucopyranuronosyl)-3-[({4-chloro-3-[5-chloro-1-(2,4-dimethoxybenzyl)-3-methyl-2-oxo-2,3-dihydro-1H-indol-3-yl]benzoyl}(ethyl)amino)methyl]pyridinium chloride The solution of 100 mg of the compound obtained in stage 3.1 in 1.6 ml of methanol is stirred at 20° C. for 15 minutes in the presence of 1 ml of sodium hydroxide (2M). 3.3 ml of hydrochloric acid (1N; pH=4) are added at 10° C. The mixture is evaporated to dryness, the residue is then purified by C18 reverse phase silica preparative chromatography, elution being carried out with an acetonitrile/water gradient from 40/60 to 80/20, and then the solution obtained is lyophilized after freezing. The expected product is obtained in the form of a white powder.

MS [(+)ESI, m/z]=780 (M$^+$).

$^1$H NMR 400 MHz (d$_6$-DMSO): 1.17 (t, 3H); 1.75 (s, 3H); 3.3-3.6 (m, 5H); 3.75 (s, 3H); 3.83 (s, 3H); 4.65-5.5 (m, 5H); 5.77 (d, 1H, J=8.51 Hz); 6.48-9.2 (m, 13H).

EXAMPLE 4

3-[({4-Chloro-3-[5-chloro-1-(2,4-dimethoxybenzyl)-3-methyl-2-oxo-2,3-dihydro-1H-indol-3-yl]benzoyl}(ethyl)amino)methyl]-1-(D-glucopyranosyl)pyridinium chloride (I): R$_0$=2-MeO; R$_1$=4-MeO; R$_2$=5-Cl; R$_3$=Me; R$_4$=4-Cl;

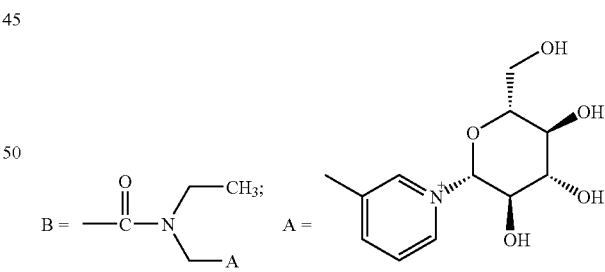

The expected product is obtained, under operating conditions analogous to those described in example 3 of the present invention, from 4-chloro-3-[5-chloro-1-(2,4-dimethoxybenzyl)-3-methyl-2-oxo-2,3-dihydro-1H-indol-3-yl]-N-ethyl-N-(pyridin-3-ylmethyl)benzamide, in the racemic form, prepared in stage 1.1, and from acetobromo-α-D-glucose.

MS [(+)ESI, m/z]=766 (M$^+$).

$^1$H NMR 400 MHz (CDCl$_3$): 1.21 (m, 3H); 1.79 (s, 3H); 3.45 (s, 2H); 3.75-4.1 (m, 12H); 4.70-5.15 (m, 4H); 5.97 (m, 1H); 6.40-9.50 (m, 13H).

EXAMPLE 5

3-[({4-Chloro-3-[5-chloro-1-(2,4-dimethoxybenzyl)-3-methyl-2-oxo-2,3-dihydro-1H-indol-3-yl]benzoyl}(ethyl)amino)methyl]-1-(D-galactopyranosyl)pyridinium chloride (I): $R_0$=2-MeO; $R_1$=4-MeO; $R_2$=5-Cl; $R_3$=Me; $R_4$=4-Cl;

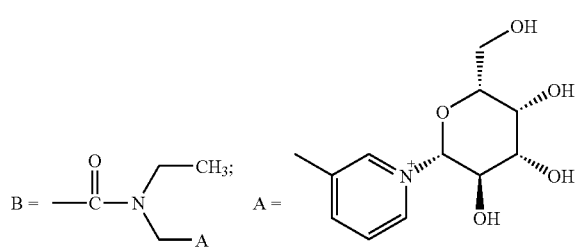

The expected product is obtained, under operating conditions analogous to those described in Example 3 of the present invention, from 4-chloro-3-[5-chloro-1-(2,4-dimethoxybenzyl)-3-methyl-2-oxo-2,3-dihydro-1H-indol-3-yl]-N-ethyl-N-(pyridin-3-ylmethyl)benzamide, in the racemic form, prepared in stage 1.1, and from acetobromo-α-D-galactose.

MS [(+)ESI, m/z]=766 (M⁺).

¹H NMR 400 MHz (CDCl₃): 1.18 (m, 3H); 1.77 (s, 3H); 3.42 (s, 2H); 3.76 (s, 3H); 3.85 (s, 3H); 2.86-4.3 (m, 6H); 4.50-5.2 (m, 4H); 5.83 (m, 1H); 6.35-9.40 (m, 13H).

EXAMPLE 6

4-Chloro-3-[5-chloro-1-(2,4-dimethoxybenzyl)-3-methyl-2-oxo-2,3-dihydro-1H-indol-3-yl]-N-ethyl-N-(1-oxypyrid-3-ylmethyl)benzamide (I): $R_0$=2-MeO; $R_1$=4-MeO; $R_2$=5-Cl; $R_3$=Me; $R_4$=4-Cl;

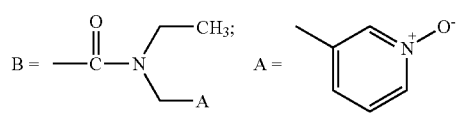

0.22 g of 3-chloroperbenzoic acid is added to 440 mg of the compound of example 201 of the document WO 01/074775 (in solution at −10° C. in 17 ml of 1,2-dimethoxyethane) and the mixture is stirred at approximately 10° C. for 16 hours. The medium is poured onto an aqueous sodium bicarbonate solution and is extracted twice with ethyl acetate. The combined organic phases are dried over sodium sulfate and then evaporated to dryness. The residue is chromatographed on a silica column, elution being carried out with a dichloromethane/methanol 99/1 to 96/4 gradient. The expected product is obtained in the base form (white resin).

M.p.=102° C.

$[\alpha]_D^{20}$=+99.4° (c=1, in MeOH).

EXAMPLE 7

4-chloro-3-[5-chloro-1-(2,4-dimethoxybenzyl)-3-methyl-2-oxo-2,3-dihydro-1H-indol-3-yl]-N-ethyl-N-(1-oxypyrid-3-ylmethyl)benzamide hydrochloride (I). Cl⁻: $R_0$=2-MeO; $R_1$=4-MeO; $R_2$=5-Cl; $R_3$=Me; $R_4$=4-Cl;

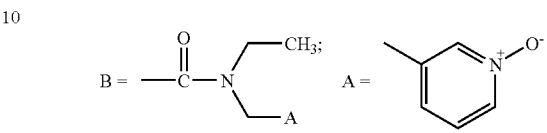

1.8 ml of a solution of hydrochloric acid (0.5M) in ethanol are added to 270 mg of the product prepared in example 6. After stirring for 1 hour, the product is filtered off, then washed with 3 ml of ethanol and subsequently dried under vacuum, and the expected salt is obtained in the form of a white powder.

M.p.=176° C.

MS [(+)ESI, m/z]=620 (MH⁺).

¹H NMR 250 MHz (d₆-DMSO): 1.17 (t, 3H); 1.75 (s, 3H); 3.25-3.4 (m, 2H); 3.77 (s, 3H); 3.84 (s, 3H); 4.60-5.1 (m, 4H); 6.48-8.45 (m, 13H).

EXAMPLE 8

(+)-4-chloro-3-[5-chloro-1-(2,4-dimethoxybenzyl)-3-methyl-2-oxo-2,3-dihydro-1H-indol-3-yl]-N-ethyl-N-[3-1-oxypyridin-4-yl)propyl]benzamide (I): $R_0$=2-MeO; $R_1$=4-MeO; $R_2$=5-Cl; $R_3$=Me; $R_4$=4-Cl;

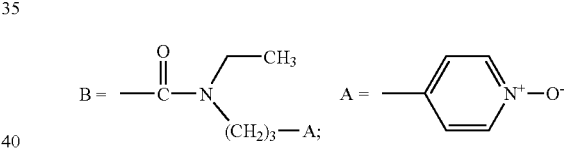

The expected product is isolated by analogy with the method of preparation of the compound of example 6 of the present invention and starting from the compound of example 204 of the document WO 01/074775.

M.p.=95° C.

$[\alpha]_D^{20}$=+97° (c=1, MeOH).

MS [(+)ESI, m/z]=648 (MH⁺).

¹H NMR 250 MHz (d₆-DMSO): 1.15 (m, 3H); 1.74 (s, 3H); 1.93 (m, 2H); 2.40-2.80 (m, 2H); 3.15-3.60 (m, 4H); 3.77 (s, 3H); 3.84 (s, 3H); 4.65-5.01 (m, 2H); 6.40-8.20 (m, 13H).

The compounds according to the invention have formed the subject of biochemical and pharmacological studies. The affinity of the compounds according to the invention for oxytocin receptors was determined in an in vitro binding test using the method described by J. Elands et al., *Eur. J. Pharmacol.* (1987), 147, pp. 197-207. This method consists in studying in vitro the displacement of a radioiodinated oxytocin analog at the oxytocin receptors in a membrane preparation of human uterine oxytocin receptors. The IC₅₀ values (concentration which inhibits 50% of the binding of the radioiodinated oxytocin analog to its receptors) are low and vary from $10^{-10}$ to $10^{-6}$ M in the latter test. By way of example, the compound of example 2 exhibits an IC₅₀ of 6.9 nM.

The compounds according to the invention are selective for oxytocin receptors.

The affinity of these compounds for human vasopressin V₁ₐ receptors (method described by M. Thibonnier et al. in *J.*

Biol. Chem. (1994), 269, pp. 3304-3310), $V_{1b}$ receptors (method described by T. Sugimoto et al. in *J. Biol. Chem.* (1994), 269, pp. 27088-27092) and $V_2$ receptors (method described by T. Birnbaumer et al. in Nature (Lond.) (1992), 357, pp. 333-335) has also been studied. The compounds studied have little or no affinity for the $V_{1a}$, $V_{1b}$ and $V_2$ receptors. By way of indication, the compound of example 7 exhibits an $IC_{50}$ of less than 50 nM with a percentage of inhibition of less 50% when it is tested at a concentration of 1 µM on the $V_{1a}$, $V_{1b}$ and $V_2$ receptors.

The agonist or antagonist nature of the compounds is determined in vitro in a test for the measurement of intracellular calcium with respect to cells expressing human oxytocin receptors according to the general technique described in *Am. J. Physiol.*, 268, and *Heart Circ. Physiol.* (1995), 37, H404-H410.

When the compounds according to the invention behave as antagonists, their $IC_{50}$ is advantageously between 0.5 µM and 0.5 nM. By way of example, the compound of example 3 is an antagonist with an $IC_{50}$ of 3 nM.

The compounds according to the invention, powerful and selective ligands of oxytocin receptors, are particularly advantageous, this being the case in the prevention and/or treatment of oxytocin-dependent disorders. The compounds according to the present invention can inhibit the effects of oxytocin.

They will be particularly advantageous in healing, in analgesia and anxiolysis (prevention of pain and anxiety), depression, schizophrenia, autism, obsessive compulsive syndrome, aggression, in maternal behavior (facilitation of mother-child recognition and acceptance) and social behavior, memory, regulation of food and drink intake, bulimia, dependence on drugs, weaning and sexual motivation. They can be advantageously used in disorders of the urogenital sphere, in particular in the obstetric and gynecological fields, in particular as uterine relaxant or tocolytic agent or for controlling contractions of the uterus before pregnancy has arrived at term, during early or premature labor in pregnant women, for controlling prenatal labor, for controlling uterine hyperactivity at the time of parturition in the event of fetal distress (Lurie et al., *Journal of Perinal Medicine* (2004), 32 (2), pp. 137-139) or for controlling preparatory labor for the purpose of a cesarian delivery, for solving problems of sterility or fertility, controlling births (in particular veterinary use), controlling estrus, the halting of breast feeding, weaning, or embryo transfer and implantation; treating endometriosis, dysmenorrhea and urinary stress or urgency incontinence, benign prostate hypertrophy and erectile dysfunctions, such as premature ejaculation, hypertension, hyponatremia, cardiac insufficiency, atherosclerosis or angiogenesis, and regulating the storage of fat by the adipocyte.

Furthermore, given the role of oxytocin in controlling luteinizing hormone (J. J. Evans, *J. Endocrin.* (1996), 151, pp. 169-174), the compounds of the invention can be used to induce contraception.

Furthermore, the compounds according to the invention can be used for their antitumor effects in oxytocin-secreting tumors, in particular breast, lung and prostate cancers. Thus, the compounds according to the invention can also be used as labels for tumors overexpressing oxytocin receptors (P. Cassoni, *Annals of Oncology* (2001), 12 (2), S37-S39, and B. Chini, *British J. of Cancer* (2003), 89, pp. 930-936).

The use of the compounds according to the invention for the prevention and/or the treatment of the abovementioned conditions in which oxytocin is implicated and for the preparation of medicaments intended to treat these conditions forms an integral part of the invention.

Another subject matter of the present invention is thus pharmaceutical compositions comprising at least one compound according to the invention and suitable excipients. Said excipients are chosen according to the pharmaceutical form and the method of administration desired: oral, sublingual, subcutaneous, intramuscular, intravenous, topical, intratracheal, intranasal, transdermal, rectal or intraocular. In particular, the intravenous method of administration can be chosen in the case of pharmaceutical compositions intended for the treatment of obstetric and gynecological disorders, such as uterine hyperactivity at the time of parturition in the event of fetal distress.

The pharmaceutical compositions are prepared according to techniques known to a person skilled in the art.

In order to obtain the desired prophylactic or therapeutic effect, each unit dose can comprise from 0.5 to 1000 mg, preferably from 1 to 500 mg, of active ingredients in combination with a pharmaceutical vehicle. This unit dose can be administered 1 to 5 times daily, so as to administer a daily dosage of 0.5 to 5000 mg, preferably of 1 to 2500 mg.

There may be specific cases where higher or lower dosages are appropriate; such dosages also come within the invention. According to normal practice, the dosage appropriate to each patient is determined by the physician according to the method of administration and the weight and the response of said patient.

The compounds according to the invention can also be used for the preparation of compositions for veterinary use intended to regulate births.

The compounds according to the invention can also be used for the preparation of cosmetic compositions. These formulations can be provided in the form of a cream for topical use and will be intended to control lypolysis, the storage of fat and cellulitis.

When a solid composition in the form of tablets is prepared, the main active ingredient is mixed with a pharmaceutical excipient, such as gelatin, starch, lactose, magnesium stearate, talc, gum arabic or the like. The tablets can be coated with sucrose, with a cellulose derivative or with other materials. The tablets can be produced by various techniques, direct tableting, dry granulation, wet granulation or hot melt.

The present invention, according to another of its aspects, also relates to a method for the treatment of the pathologies indicated above which comprises the administration of a compound according to the invention or one of its pharmaceutically acceptable salts.

What is claimed is:
1. A compound of formula (I):

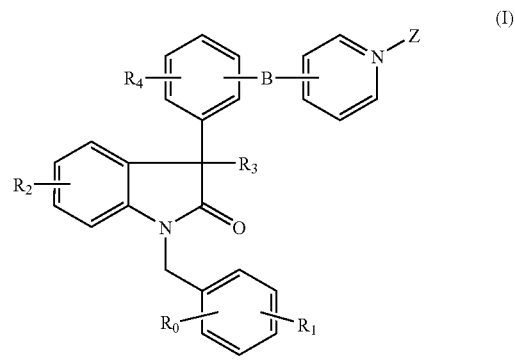

wherein:
$R_0$ represents a hydrogen atom, a halogen atom, a $(C_1\text{-}C_6)$ alkyl group or a $(C_1\text{-}C_6)$alkoxy group;
$R_1$ represents a hydrogen atom, a halogen atom, a $(C_1\text{-}C_6)$ alkyl group or a $(C_1\text{-}C_6)$alkoxy group;
$R_2$ represents a hydrogen atom, a halogen atom, a $(C_1\text{-}C_6)$ alkyl group or a $(C_1\text{-}C_6)$alkoxy group;
$R_3$ represents a hydrogen atom or a $(C_1\text{-}C_6)$alkyl group;

R₄ represents a hydrogen atom, a halogen atom, a ($C_1$-$C_6$) alkyl group or a ($C_1$-$C_6$)alkoxy group;

Z represents a tetrahydrofuranyl group or a tetrahydropyranyl group, said groups optionally being substituted by one or more ($C_1$-$C_3$)alkyl, hydroxyl or carboxyl groups or a —$CH_2OH$ group;

B represents a T-W group, in which:

T represents a —$(CH_2)_m$— group, in which m is equal to 0 or 1;

W represents:
a —$CONR_6R_7$ group, in which:
$R_6$ represents a hydrogen atom or a ($C_1$-$C_6$)alkyl group,
$R_7$ represents a ($C_1$-$C_6$)alkylene group;
or W represents an —$NR_8COR_9$ group, in which:
$R_8$ represents a hydrogen atom or a ($C_1$-$C_6$)alkyl group,
$R_9$ represents a —$(CH_2)_n$-group, in which n is a value selected from 0 to 3;
or a racemic mixture, enantiomer, or diastereoisomer of said compound, or a mixture thereof;
or a pharmaceutically acceptable salt thereof.

2. The compound of formula (I) as claimed in claim 1, wherein:
$R_0$ represents a ($C_1$-$C_6$)alkoxy group;
$R_1$ represents a ($C_1$-$C_6$)alkoxy group;
$R_2$, $R_3$, $R_4$, Z and B are as defined in claim 1;
or a racemic mixture, enantiomer, or diastereoisomer of said compound, or a mixture thereof;
or a pharmaceutically acceptable salt thereof.

3. The compound of formula (I) as claimed in claim 1, wherein:
$R_0$ represents a hydrogen atom, a halogen atom, a ($C_1$-$C_6$) alkyl group or a ($C_1$-$C_6$)alkoxy group;
$R_1$ represents a hydrogen atom, a halogen atom, a ($C_1$-$C_6$) alkyl group or a ($C_1$-$C_6$)alkoxy group;
$R_2$, $R_3$, $R_4$ and B are as defined in claim 1;
Z represents an oxygen atom;
or a racemic mixture, enantiomer, or diastereoisomer of said compound, or a mixture thereof;
or a pharmaceutically acceptable salt thereof.

4. The compound of formula (I) as claimed in claim 1, in which:
$R_0$ represents a hydrogen atom, a halogen atom, a ($C_1$-$C_6$) alkyl group or a ($C_1$-$C_6$)alkoxy group;
$R_1$ represents a hydrogen atom, a halogen atom, a ($C_1$-$C_6$) alkyl group or a ($C_1$-$C_6$)alkoxy group;
$R_2$, $R_3$, $R_4$ and B are as defined in claim 1;
Z represents a tetrahydrofuranyl group or a tetrahydropyranyl group, said groups optionally being substituted by one or more ($C_1$-$C_3$)alkyl groups, a hydroxyl or carboxyl group or a —$CH_2OH$ group;
or a racemic mixture, enantiomer, or diastereoisomer of said compound, or a mixture thereof;
or a pharmaceutically acceptable salt thereof.

5. The compound as claimed in claim 1, selected from the group consisting of:
1-(β-D-glucopyranuronosyl)-3-[({4-chloro-3-[5-chloro-1-(2, 4-dimethoxybenzyl)-3-methyl-2-oxo-2,3-dihydro-1H-indol-3-yl]benzoyl}(ethyl)amino)methyl]pyridinium chloride;
3-[({4-chloro-3-[5-chloro-1-(2,4-dimethoxybenzyl)-3-methyl-2-oxo-2,3-dihydro-1H-indol-3-yl]benzoyl} (ethyl)amino)methyl]-1-(D-glucopyranosyl)pyridinium chloride; and
3-[({4-chloro-3-[5-chloro-1-(2,4-dimethoxybenzyl)-3-methyl-2-oxo-2,3-dihydro-1H-indol-3-yl]benzoyl} (ethyl)amino)methyl]-1-(D-galactopyranosyl)pyridinium chloride.

6. A process for the preparation of a compound of formula (I) as claimed in claim 1, wherein the compound of formula (II):

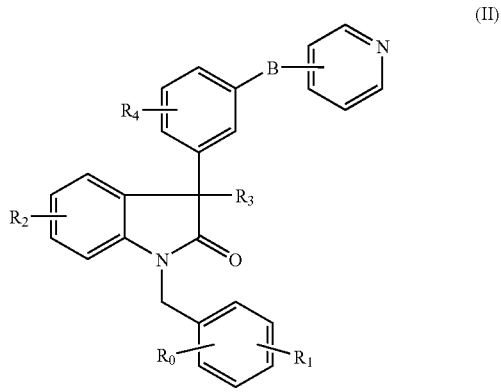

(II)

in which $R_0$, $R_1$, $R_2$, $R_3$, $R_4$ and B are as defined in claim 1, is reacted with a compound of formula Z-X, in which Z is as defined in claim 1 and X represents a leaving group.

7. A pharmaceutical composition comprising one or more compound according to claim 1 and a suitable excipient.

8. A pharmaceutical composition comprising one or more compound according to claim 2 and a suitable excipient.

9. A pharmaceutical composition comprising one or more compound according to claim 3 and a suitable excipient.

10. A pharmaceutical composition comprising one or more compound according to claim 4 and a suitable excipient.

11. A pharmaceutical composition comprising one or more compound according to claim 5 and a suitable excipient.

* * * * *